United States Patent [19]

Pankow

[11] Patent Number: 5,529,678
[45] Date of Patent: *Jun. 25, 1996

[54] LENS DECONTAMINATION SYSTEM

[75] Inventor: Mark L. Pankow, Chicago, Ill.

[73] Assignee: Isoclear, Inc., Chicago, Ill.

[ * ] Notice: The term of this patent shall not extend beyond the expiration date of Pat. No. 5,368,708.

[21] Appl. No.: 333,794

[22] Filed: Nov. 3, 1994

Related U.S. Application Data

[63] Continuation of Ser. No. 90,293, Jul. 12, 1993, Pat. No. 5,368,708, which is a continuation-in-part of Ser. No. 800,686, Dec. 2, 1991, Pat. No. 5,227,039.

[51] Int. Cl.$^6$ .................. G01N 27/26; G01N 27/453
[52] U.S. Cl. .................. 204/600; 204/450; 204/456; 204/606
[58] Field of Search .................. 204/299 R, 180.1; 134/1, 901; 422/22

[56] References Cited

U.S. PATENT DOCUMENTS

| Re. 32,672 | 5/1988 | Huth et al. | 252/95 |
|---|---|---|---|
| 2,843,540 | 7/1958 | Ressler | 204/180 |
| 2,932,383 | 4/1960 | Fagan | 206/5 |
| 3,037,616 | 6/1962 | Phipps, III | 206/5 |
| 3,054,412 | 9/1962 | Nickell | 134/137 |
| 3,083,819 | 4/1963 | Entzminger | 206/5 |
| 3,089,500 | 5/1963 | Stalcup | 134/156 |
| 3,149,364 | 9/1964 | Baptist et al. | 15/506 |
| 3,317,417 | 5/1967 | Raymond | 204/299 |
| 3,344,461 | 10/1967 | Floor | 15/512 |
| 3,369,656 | 2/1968 | Skinner | 206/56 |
| 3,494,846 | 2/1970 | Arquembourg | 204/180 |
| 3,725,226 | 3/1973 | Stoner | 204/149 |
| 3,764,513 | 10/1973 | Saravis | 204/299 |
| 3,808,118 | 8/1974 | Golias | 204/299 |
| 3,871,395 | 3/1975 | Murry | 134/107 |
| 3,896,021 | 7/1975 | Fosslien | 204/299 |
| 3,908,680 | 9/1975 | Krezanoski | 134/27 |
| 3,930,973 | 12/1975 | Nerenberg | 204/180 |
| 3,962,069 | 6/1976 | Inoue et al. | 204/300 |
| 3,977,517 | 8/1976 | Kadlecik et al. | 206/5.1 |
| 3,990,579 | 11/1976 | Manning | 206/501 |

(List continued on next page.)

FOREIGN PATENT DOCUMENTS

| 0268087 | 5/1988 | European Pat. Off. . |
| 3-148624 | 6/1991 | Japan . |
| 3-171032 | 7/1991 | Japan . |

OTHER PUBLICATIONS

"Cleaning Hydrophilic Contact Lenses: An Overview" by Stuart Eriksen, *Annals of Ophthalmology*, Sep. 1975, pp. 1223–1232.

"The Effect on Measured Visual Acuity of Protein Deposition and Removal in Soft Contact Lenses" by David A. McClure et al., *Contacto*, Mar. 1977, pp. 8–12.

"Deposits on Soft Contact Lenses, Electrophoresis and Scanning Electron Microscopic Examinations" by T. Bilbaut et al., *Exp. Eye Res*, 1968, pp. 153–165.

"Protein Migration Through Hydrogels: A Tool for Measuring Porosity—Application to Hydrogels Used as Contact Lenses" by A. M. Gachon et al. *Analytical Biochemistry*, (1968), pp. 249–255.

"Identification Prevention and Removal of Contact Lens Deposits", (booklet) *Optometry Documenta*, (1984).

Primary Examiner—John Niebling
Assistant Examiner—John S. Starsiak, Jr.
Attorney, Agent, or Firm—Lockwood, Alex, Fitzgibbon & Cummings

[57] ABSTRACT

A system by which contaminants from and below the surface of contact lenses may be electrokinetically removed. The system includes a protective encasement packet in which a lens is safely protected upon its removal from the eye, through the cleaning procedure, and until the lens is returned to the eye. The system includes also a cleaning assembly in which the lens as encased within the packet is decontaminated. The cleaning assembly includes surfaces positionable to contact the packet and from which electrical charges are transmitted to the lens. Under the influence of the electrical charges, contaminants are drawn off of and from below the surface of the lens.

22 Claims, 3 Drawing Sheets

U.S. PATENT DOCUMENTS

| | | | |
|---|---|---|---|
| 4,096,870 | 6/1978 | Manfuso, Jr. | 134/28 |
| 4,187,574 | 2/1980 | Wrue | 15/104.92 |
| 4,202,740 | 5/1980 | Stoner et al. | 204/130 |
| 4,223,782 | 9/1980 | Giambalvo | 106/3.1 |
| 4,263,054 | 4/1981 | Giambalvo | 134/21 |
| 4,357,173 | 11/1982 | Rosenthal et al. | 134/6 |
| 4,444,307 | 4/1984 | Jermyn | 206/5.1 |
| 4,493,783 | 1/1985 | Su et al. | 252/174.23 |
| 4,533,399 | 8/1985 | Mencke | 134/6 |
| 4,559,662 | 12/1985 | Kunold, Jr. | 15/104.94 |
| 4,582,076 | 4/1986 | Prat | 134/57 R |
| 4,607,652 | 8/1986 | Yung | 134/184 |
| 4,608,147 | 8/1986 | Clad | 204/301 |
| 4,609,493 | 9/1986 | Schafer | 252/546 |
| 4,613,379 | 9/1986 | Su et al. | 134/7 |
| 4,615,786 | 10/1986 | Culkin et al. | 204/301 |
| 4,619,747 | 10/1986 | Hoadley et al. | 204/182.8 |
| 4,631,120 | 12/1986 | Pohl | 204/182.8 |
| 4,668,359 | 5/1987 | Postle et al. | 204/182.7 |
| 4,732,185 | 5/1988 | Cowle et al. | 134/84 |
| 4,792,414 | 12/1988 | Su et al. | 252/174.12 |
| 4,839,082 | 6/1989 | Bhatia | 252/174.12 |
| 4,840,681 | 6/1989 | Pompe | 134/42 |
| 4,852,592 | 8/1989 | DiGangi et al. | 134/57 |
| 4,872,965 | 10/1989 | Pankow | 204/299 |
| 4,998,590 | 3/1991 | Glorieux | 21/89 |
| 5,017,238 | 5/1991 | Chromecek | 134/7 |
| 5,037,484 | 8/1991 | Su et al. | 134/7 |
| 5,037,485 | 8/1991 | Chromecek et al. | 134/7 |
| 5,054,610 | 10/1991 | Ajello | 206/5.1 |
| 5,071,276 | 12/1991 | Nielsen et al. | 401/9 |
| 5,073,202 | 12/1991 | Wallach | 134/6 |
| 5,100,477 | 3/1992 | Chromecek et al. | 134/7 |
| 5,114,686 | 5/1992 | Gillespie | 422/300 |
| 5,127,126 | 7/1992 | Tanaka et al. | 15/214 |
| 5,128,058 | 7/1992 | Ishii et al. | 252/174.13 |

LENS DECONTAMINATION SYSTEM

This is a continuation of application Ser. No. 08/090,293, filed Jul. 12, 1993, now U.S. Pat. No. 5,368,708, which is a continuation-in-part of application Ser. No. 800,686, filed Dec. 2, 1991, now U.S. Pat. No. 5,227,039.

BACKGROUND OF THE INVENTION

The present invention generally relates to a system for decontaminating contact lenses. More particularly, the invention relates to a system with the use of which contaminants can be removed from and below the surface of contact lenses. Advantageously, the system includes an apparatus of a simplified construction by which a lens can be decontaminated efficiently.

A contact lens is a small, shell-shaped device having a dominant concave surface and a dominant convex surface meeting at a surrounding edge. In addition to being used generally to correct refractive errors of the eye on which the lens is placed, contact lenses may be worn also for cosmetic purposes.

Contact lenses can be made of a variety of materials. Glass is one type of such material. However, to provide a lens that does not easily crack, that is light, and that easily conforms to the cornea, groups of materials other than glass are now largely used to make contact lenses. Plastic materials, such as hydrogel plastics are one group of such materials widely used to make lenses. Hydrogel plastics have the unique property of being able to absorb and bind a proportionality large amount of water within a polymer network. A very flexible and soft structure results. Lenses made from hydrated hydrogel plastics are comfortable to wear because their softness allows them to easily conform to the cornea of the eye.

However, regardless of the material from which they are made, contact lenses are susceptible to contamination. A lens in place on the eye readily collects the oily and sebaceous substances and protein secreted by the eye. A lens positioned on the eye can collect also airborne chemicals and biological agents such as bacteria, viruses, and fungus. Furthermore, the simple handling of the lens by the user, such as during the placement of or the adjustment of the lens on the eye, can place a variety of foreign organic and inorganic substances on the lens.

Contaminants largely collect at the surface of lens. However, the hydrated polymer subsurface network of those lenses made from hydrogel plastics allow water-soluble substances and ions to readily enter and become lodged below the surface of these lenses.

The rate at which contaminants can accumulate on and in a lens is variable but generally rapid. It has been found that fifty percent of a lens surface may be covered by deposits after only a half-hour of lens wear. Within 8 hours, ninety percent of the lens surface may be coated. Complete coverage occurs typically within a matter of weeks. With time, new layers of contaminants form on the older layers of contaminants that were not removed by conventional cleaning methods. The contamination coating simply thickens.

Lens contaminants affect the optical performance of a lens. Sufficient layers of contaminants can accumulate on and within the lens to form a colored and/or partially opaque layer of oil, mucous, and crystalline deposits. The amount of light transmitted through the lens—and, therefore, visual acuity—diminishes depending on the composition, thickness, and extent of the contamination coating.

Lens contaminants affect also the mechanical performance of a lens. Lenses coated with a layer of contaminants can roughen the surface of a lens thereby transforming a smooth, easy-to-wear device to a roughened source of irritation. Rather than softly sitting on the cornea and allowing the eyelid to smoothly glide across its surface, the lens may cause abrasions and possible giant papillary conjunctivitis.

Sufficient amounts of contamination can ultimately affect the physiological compatibility of the lens with eye. The "tear exchange" and the oxygen exchange of the lenses with the eye may be decreased by increased amounts of foreign deposits on the lenses. A hydrogel lens that does not provide sufficient oxygen to the cornea can cause edema and corneal thickening. A coating of contaminants on a lens can also serve as an environment in which microorganisms, such as bacteria, fungi, and yeast, can flourish. Conditions such as conjunctivitis may result.

A variety of agents and techniques directed to the removal of lens contaminants are known. However, their usefulness is generally limited. Known agents and techniques are typically directed to the removal of only one or a few types of contaminants from the surface of a lens.

To illustrate this point, lenses are commonly cleaned with surfactants, oxidants, disinfectants, enzymatic cleaners, or abrasive, alone or in combination, and/or with the assistance of some additional cleaning technique and/or piece of apparatus. Surfactants are directed primarily to emulsifying and displacing more loosely bound layers of debris from the surface of the lens. Surfactant-based cleaners, however, cannot generally dislodge more tightly bound contaminants and/or those deposits that may have become denatured such as during an earlier cleaning attempts.

Oxidants are largely directed to disinfecting lenses, that is, the killing of any bacteria that can be reached by the oxidant. One form of oxidant is hydrogen peroxide. However, oxidants must be thoroughly removed from the lens before it is returned to the eye. Oxidants that come into contact with the cornea can cause stinging, tearing, photophobia, and, if in high enough concentrations or if allowed to maintain prolonged contact with the cornea, cellular damage.

Other disinfectants are known. However, many such chemical disinfectants can be absorbed by the lens and, if not removed prior to the placement of the lens back onto the eye, may also cause damage to it.

Enzymatic cleaners are used to remove the protein from lenses. Enzymatic cleaners utilize proteolytic-enzymes, such as papain, pancreatin, or subtilisin, to break up protein contaminants into water soluble pieces. Enzymatic cleaners are generally considered to be more effective than surfactant-based cleaners in accomplishing this specialized task. However, after lenses have been cleaned with these cleaners, they must be deactivated. Any enzymes remaining in the lens may attack the protein surface of the eye. Accordingly, enzymatic cleaning requires additional treatment steps, such as the application of hydrogen peroxide to the lens to deactivate the enzymes and then the removal of the hydrogen peroxide from the lens such as by rinsing.

Abrasives are directed to the removal of contaminants from the surface of the lens. Lens wearers typically work the abrasive manually over the surface of the lens until the wearer is satisfied that the lens is cleaned. Abrading away contaminants damaging the lens during the handling process, however, requires great physical dexterity on the part of the user. This is particularly true when the cleaning of lenses made from the softer plastic materials is attempted. Such lenses scratch easily. Furthermore, abrasive cleaning agents, as other cleaning agents, must be entirely removed from the lens before it is returned to the eye. Abrasive that are allowed to remain on the lens will cause abrasions and irritation to the cornea or eyelid.

Conventional cleaning agents are largely ineffective in removing all or even most of those contaminants which they are intended to remove. Because of this inefficiency, mechanical devices are often used in combination with the cleaning agents to improve their efficacy. Such mechanical devices vibrate, rotate, scrub, heat, agitate and/or direct ultrasonic waves to a lens in an attempt to further dislodge and/or deactivate the elements fouling the lens.

It has been estimated that, at a maximum, some fifty percent of the contaminants remain on the lens after the use of conventional cleaning agents and methods. Contaminants absorbed below the surface of the lens and within the polymer network of hydrogel lenses are largely unaffected by most of these techniques. In fact, some of the techniques actually exacerbate the contamination problem by denaturing the protein component of the contamination coating so that it forms an intractable layer. As a result, even by following recommended known cleaning procedures, the contamination layer gradually extends and thickens. Because of the increased irritation and the decreased visual acuity caused by this layer, lenses must eventually be discarded for new lenses. Typically, the replacement of lenses is required within one year.

A demand, therefore, exists for apparatus and methods by which a wide range of contaminants can be removed effectively and safely from contact lenses. The present invention satisfies the demand.

The present invention relies on the following principles and novel findings. Substances present in an aqueous environment, such as the contaminants deposited on and absorbed below the surface of a lens, have a surface electrical charge. Some contaminants have a positive surface charge while others have a negative surface charge. It has been found that by applying separate electrical charges to the lens these charged contaminants move to and/or off the surface of a lens and in a direction toward that charge that is opposite the charge which the contaminant has.

The present invention utilizes these principles and findings to decontaminate contact lens efficiently and safely. The novel apparatus of the present invention includes circuitry by which opposite charges can be produced on either side of a lens to electrokinetically draw contaminants from within and off of the lens.

Compared to some conventional cleaning agents, apparatus, and techniques, that kill or denature, but do not remove more than a limited percentage of contaminants from a lens, the present invention advantageously removes a large percentage of or all of the contaminants from a lens. Further, compared to other conventional cleaning, agents, apparatus, and techniques that generally kill, denature, and/or remove only certain of the contaminants present on the surface of the lens, the present invention further advantageously dislodges generally all of the contaminants from the surface of the lens. Additionally, compared to conventional cleaning agents, apparatus, and techniques that generally are unable to remove contaminants from below the surface of a lens, the present invention removes also these contaminants.

While contaminants removed by the use of conventional apparatus are allowed to freely come in contact with, and thereby possibly infect or contaminate the surfaces of the apparatus, the present invention includes novel means to prevent the dispersal of the lens contaminants. The present invention utilizes a protective encasement packet. The protective encasement packet is of a structure and is composed of a substance or substances such that the lens can be protected within it upon the lens' removal from the eye, through the cleaning process, and until the lens is readied for return to the eye. The protective encasement packet structure and composition facilitates the complete application of the electrical charges to the entire lens surface during the cleaning process. Contaminants removed from the lens during the cleaning stage are trapped and prevented from coming in contact with the surface of the apparatus. Advantageously, the need for post-procedure sterilization or extensive cleaning of the apparatus is obviated.

To clean a lens according to the present invention, the lens, upon its removal from the eye, is inserted within a protective encasement packet. The packet, within which the lens is safely encased, is positioned in a cleaning assembly according to the present invention. The cleaning assembly includes charge transmitting areas having surfaces that are positionable to either side of the lens within the packet. Opposite charges are produced in each of the charge transmitting areas. Contaminants at and below the surface of the lens are drawn toward the charge transmitting area having that charge that is opposite to the charge that the contaminant has. Those contaminants drawn off the lens surface are advantageously trapped within the protective encasement packet. In one preferred embodiment of the present invention, the protective encasement packet is made from a relatively inexpensive substance or substances such that the packet, and those contaminants trapped within it, may be discarded upon completion of the lens cleaning operation. Any contaminants dislodged to and at the surface of the lens can be easily removed from it, such as by rinsing.

Removal of generally all of the contaminants from a lens prevents the gradually increasing irritation of the eye caused by lenses that have been incompletely cleaned.

Removal of generally all of the contaminants from a lens is further advantageous in that it extends the life of a lens. Lenses cleaned with conventional cleaning agents and techniques must be discarded within a short period of time, such as a year, because of the increased irritation and decreasing visual acuity caused by the contamination build-up.

The present invention is advantageous also in that it is safe to the lens. Conventional cleaning agents and methods generally include one or more steps during which the possibility that the lens may be damaged is heightened. For example, one widely used technique in which an abrasive is used to clean a lens generally requires extensive handling of the lens during the entire cleaning operation. The lens may be harmed by mishandling and/or by the overzealous application of the abrasive to the lens surface.

Other conventional cleaning techniques require that the lens be placed into various containers or devices made of several pieces and/or having doors, covers, or lids that must be fitted, snapped, screwed, or closed shut. Often times these same containers are fitted into or form a part of an apparatus that rotates, spins, vibrates, heats, etc. the lens. The lens may be punctured, scratched, compressed, snipped, or otherwise damaged during the fitting, snapping, screwing, or closing shut of the lens container and/or during the prolonged exposure of the lens to conventional cleaning techniques.

Cleaning a lens with the present invention advantageously does not require the use of conventional containers and avoids the possibly dangerous prolonged unprotected exposure of the lens. The user simply removes the lens from his or her eye and inserts it into the protective encasement packet. The portion of the protective packet with which the lens may make contact during its insertion is generally soft and pliable so that the lens cannot thereby be scratched or damaged. As securely encased in the protective packet, the lens is positioned in the cleaning assembly. The charge transmitting areas are positioned to contact the packet such that opposing electrical charges are transmitted to the lens within the protective packet. Upon completion of the application of the electrical charges, the lens is still secured in the protective packet is withdrawn from the cleaning assembly. During the removal of the lens from the protective packet, soft and pliable substances within the protective packet may contact the lens. Accordingly, the possibility that the lens may be damaged during the cleaning procedure of the present invention is largely avoided.

Some conventional cleaning procedures may further require the consumer to coordinate the use of, for example, solutions, fluids, tablets, containers, and/or other complex, multiple component apparatus in what may be time-consuming procedures. Coordinating the use of many components and/or a complex apparatus is not a simple task especially by a consumer that has removed his or her lenses for cleaning.

The present invention provides advantageously an apparatus also of a simplified construction by which lenses can be cleaned simply, efficiently, and without the complicated procedures of known techniques. According to the present invention, the user places his or her lens in the protective encasement packet. The packet is easy to use even by those with temporarily limited vision caused by the removal of his or her lens. The packet is placed in the cleaning assembly. The lens, as encased in the protective packet, is subjected to electrical charges for a limited period of time. After the application of electrical charges, the packet is removed. The lens is removed from the packet and may be, after, for example, rinsing and soaking in saline solution, placed back onto the eye. Because the packet includes a substance that is in generally complete contact with the lens surface, the charges are applied to the entire lens surface. Accordingly, the lens is entirely cleaned and the partial cleaning or shadow effects of conventional apparatus and methods is avoided.

The present invention provides also apparatus and methods by which lenses may be cleaned inexpensively. Many conventional cleaning devices and techniques require the consumer to purchase once, or on an ongoing basis, solutions, fluids, tablets, containers, and/or other apparatus. In contrast, the present invention utilizes a cleaning housing and a protective encasement packet. The protective encasement packet may be made from components that may be reused. Additionally, the protective encasement packet may be made partially or entirely, from components that are generally inexpensive. Advantageously, a packet made from such materials may be discarded after a single use rather than cleaned and reused.

Additionally, the present invention does not require the great amount of time to set up and actually clean a lens as known apparatus and methods do. Compared to known apparatus and methods, lenses can be cleaned by the present invention in significantly less time and, generally, in minutes.

The present invention specifically overcomes the disadvantages of the conventional apparatus and methods that require also the coordinated use of fluid, containers for holding the fluid, containers in which lens or lenses must be retained so that the lens can be held under the surface of the body of fluid, and the application of electrical charges through the fluid and containers.

It is, accordingly, a general object of the present invention to provide apparatus and methods by which contaminants may be removed from contact lenses.

Another object of the present invention is to provide apparatus and methods by which contaminants may be removed from contact lenses safely and with minimal exposure and danger to the lens.

A further object of the present invention is to provide apparatus and methods by which contaminants may be removed from lenses simply and without the need to coordinate the use of multiple components in a complex cleaning procedure.

An additional object of the present invention is to provide apparatus and methods by which contaminants may be removed from contact lenses by the application of opposite electrical charges to the lens.

A further object of the present invention is to provide apparatus and methods by which contaminants may be removed from contact lenses and onto protective means to lessen the likelihood of exposure of the circuitry and the device in which it is held to the contaminants.

An added object of the present invention is to provide apparatus and methods by which contaminants may be removed quickly and generally in minutes.

These and other objects, features, and advantages of this invention will be clearly understood and explained with reference to the accompanying drawings and through a consideration of the following detailed description of the preferred embodiments.

DESCRIPTION OF THE PREFERRED EMBODIMENTS

Figure 1:
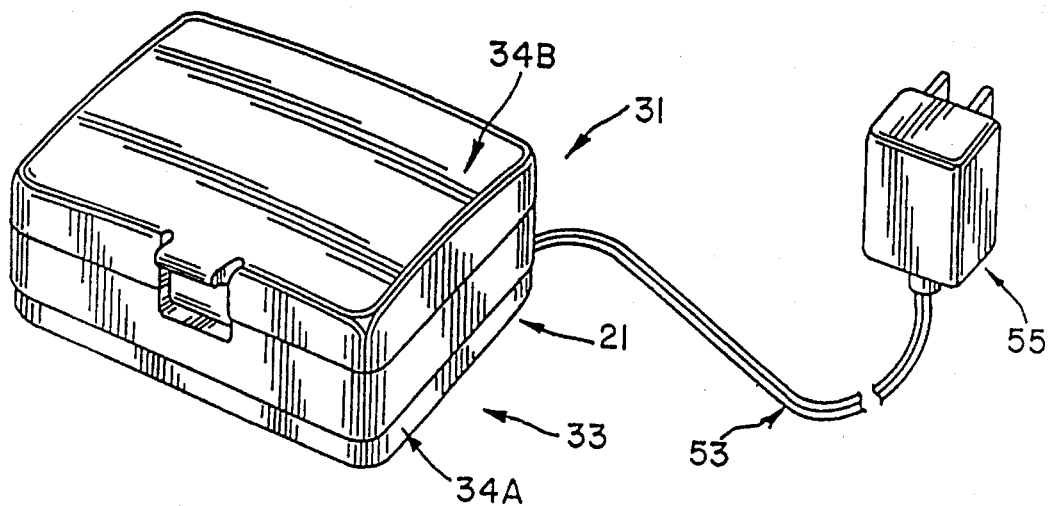
FIG. 1 is a perspective view of one embodiment of the cleaning assembly of the present invention in a closed position.

A lens decontamination system according to the present invention is designated in FIGS. 1 through 6 as 21. Lens cleaning system 21 includes circuitry 51 by which electrical charges are produced and a packet 81 through which the electrical charges are transmitted to a lens protectively encased within the packet 81 to electrokinetically decontaminate the lens. To facilitate the decontamination of one or more lenses protectively encased within an equal number of packets 81 by the charges produced by circuitry 51, one embodiment of the present invention includes a housing 33.

Housing 33 is made from non-conductive and durable material or combination of materials such that housing does not accidentally conduct electricity and is of a thickness or strength such that the housing 33 can withstand normal consumer usage without breakage. Furthermore, in order to minimize the amount of time needed to maintain it in a clean condition, housing 33 preferably has an exterior construction having a limited number of crevices or areas in which dirt may collect or bacteria may flourish. The embodiment of the housing 33 illustrated in the attached Figures includes such an exterior construction. The illustrated embodiment is advantageous also in that sharp edges and corners are largely eliminated to provide an inherently safe shape.

Within housing 33, circuitry 51 is assembled. Circuitry 51 is preferably insulated and sealed within housing 33 so that the circuitry cannot be adversely affected by contact with fluids and/or prolonged contact with the atmosphere. Circuitry 51 operates to generate electrical charges of sufficient voltage and amperage to clean one or more lenses 101 encased within one or more protective encasement packets 81.

Circuitry 51 preferably operates on a low voltage, low amperage current. Low voltage, low amperage current is preferred for reasons of safety—not only to protect the user of the system in case of accidental contact, but also to prevent any damage to the lens being cleaned. Power may be supplied through a lead 53 from a power pack 54 connected to a standard house current through plug 55 or from batteries (not shown).

Circuitry 51 produces the electrical charges at charge transmitting areas 61. The charge transmitting areas 61 are of a structure to facilitate the transfer of electrical charges to a protective encasement packet 81 in which a lens is held. Charge transmitting areas 61 are preferably made of a material or materials that are efficient conductors. Suitable materials from which charge transmitting areas 61 may be made include conductive materials such as conductive metals, alloys, and composites. Platinum, iron alloys such as stainless steel, graphite, and graphite fiber-polymer composites are some such conductive materials. It is preferred that charge transmitting areas 61 are separate areas 61A, 61B at which charges having opposite polarity can be developed. So that more than one lens may be cleaned simultaneously, circuitry 51 may include a set of charge transmitting areas 61A, 61B for each of a pair of lens. In the embodiment illustrated in FIGS. 2 through 6, the assembly 31 includes two sets of charge transmitting areas 61A, 61B thereby allowing two lenses to be decontaminated simultaneously.

In one embodiment, the polarity of each charge transmitting area 61A, 61B remains the same during the decontamination process. In another embodiment, the polarity of the charges developed at each charge transmitting area 61A, 61B is alternated while the lens is being decontaminated. Circuitry 51 by which the polarity of the charges developed at charge transmitting areas 61A, 61B are periodically alternated is advantageous for a number of reasons including the following. Alternately presenting positive and negative charges to each of the dominant convex and concave sides and surrounding edge of a lens, thereby ensures that both positively and negatively charged contaminants are thoroughly removed from both sides and the edge area of the lens. Furthermore, it is known that biological agents, such as bacteria, are killed when subjected to alternating charges.

The charge transmitting areas 61 may include additional structure and shape and further composition to facilitate contact with and efficiently transmit electrical charges to a protective encasement packet 81. In the illustrated embodiment, charge transmitting areas 61 includes a charge transmitting surface 62 across which the outer face 86 of the protective encasement packet 81 may be contacted to effect the transmission of the electrical charge. This surface 62, as may be other portions of the charge transmitting areas 61, may be raised or depressed in relationship to housing surface 35. This surface 62, as other portions of the charge transmitting areas 61, may have also an angular, spherical, flat, or any single or combined shapes to facilitate the efficient transmission of electrical charges to the protective encasement packet 81. In the embodiments of the cleaning assembly 31 illustrated in FIGS. 2 through 5, charge transmitting areas 61 are of uniform construction.

While the charge transmitting surfaces 62 may be of the same material as the charge transmitting areas 61, charge transmitting surface 62 may also be of different material integrated with, connected to, or forming a layer on other sections of the charge transmitting area 61.

While many materials may be suitable for conducting a charge, these same materials may not necessarily be suitable for constant exposure as a charge transmitting surface 62 without, for example, being rapidly oxidized. Accordingly, it is preferred that at the least charge transmitting surface 62 be made from a material that does not readily oxidize when exposed to normal atmospheric conditions and used according to the present invention. Such materials include some metals and metal alloys—for example, platinum and stainless steel. A material such as stainless steel is advantageous, not only because it less expensive than platinum but also because it may be easily cleaned, such as by wiping.

Charge transmitting areas 61A, 61B are exposed from a surface 35 of housing 33. In order to facilitate the positioning of the charge transmitting areas 61A, 61B on either side of the protective encasement packet 81 in which a lens 101 is encased, one preferred embodiment of the housing 33 includes separate housing elements 34A, 34B having separate moveable surfaces 35A, 35B positionable in relationship to each other. In the illustrated embodiment of the housing 33 shown in the Figures, housing element 34A is structured to form a bottom 38—by which element 34A, and thereby the entire housing 33 may be stably positioned on a generally horizontal and flat surface. In the illustrated embodiment, housing element 34B forms a cover. In use, housing element 34A would rest for example, on a horizontal space, such as a counter, and surface 35A would form, in relationship to surface 35B, a lower surface.

In the illustrated embodiment, the separate lower surface 35A and an upper surface 35B are moveable in relationship to each other so that advantageously charge transmitting surfaces 62A are alignable opposite to charge transmitting surfaces 62B such that a space 91 is provided therebetween. This space 91 is of a size such that a protective encasement packet 81 can be fitted therein and can be contacted by charge transmitting surface 62A and a charge transmitting surface 62B and without distorting or causing damaging compression of the lens.

While the cover 34B can be separate from and be attachable to element 34A—such as by fitting the cover 34B over element 34A, housing 33 also may include means by which the housing elements 34A, 34B may be pivotally positioned with respect to each other to form accommodation space 91. Such positioning means may include a hinge 41. Hinge 41 may include a spring arrangement by which the positioning of the elements 34A, 34B may be varied in order to provide space 91 of varying depth in order to accommodate packets 81 of varying thickness.

The embodiment of the cleaning assembly 31 shown in FIGS. 2 through 5 advantageously facilitates the positioning of two packets 81, each of which may contain a contact lens, on and between a separate set of charge transmitting surfaces 62A, 62B. In relationship to surface 35A, charge transmitting surfaces 62A of this embodiment are depressed while charge transmitting surfaces 62B are raised in relationship to surface 35B.

Preferably, the housing 33 and the protective encasement packet 81 each are of a cooperative structure so that the electrostatic field developed between each set of the charge transmitting surfaces 62A, 62B and through each packet 81 and through each lens 81 is optimally maximized given the preferred use of a low amperage current to develop the charges. The electrostatic field can be optimally maximized, such as by increasing the area of the charge transmitting surface 62. The electrostatic field can be optimally maximized also by decreasing the space 91 between each the charge transmitting surface 62A, 62B when the surfaces are aligned opposite to each other. At a minimum, the space must accommodate a protective encasement packet without causing damaging compression of the lens contained therein. In those embodiments of the assembly 31 including two sets of charge transmitting surfaces, the total capacitance can be increased by connecting each set of charge transmitting areas 61A, 61B and 62A, 62B, in a parallel connection circuit.

Figure 4:
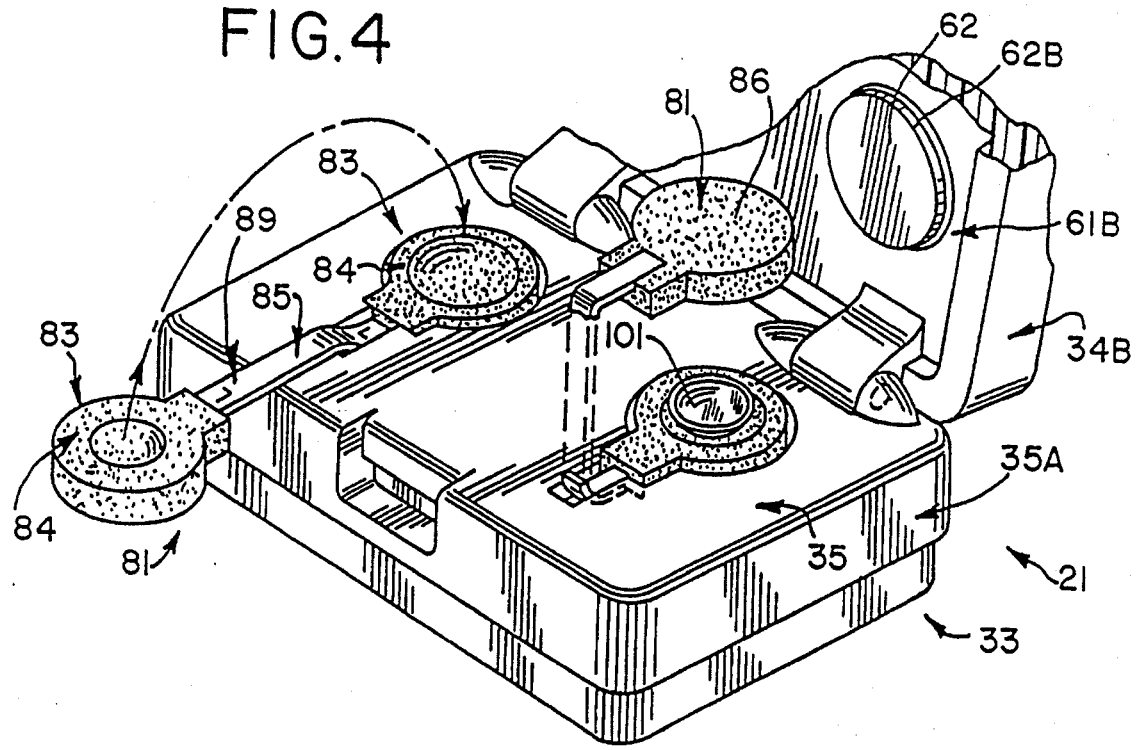
FIG. 4 is a partial perspective view of the embodiment of cleaning assembly illustrated in the above Figures and showing one embodiment of a protective encasement packet positioned as a pair on charge transmitting surfaces of the cleaning assembly, and a lens aligned on one of the inner faces of the packet.
Figure 5:
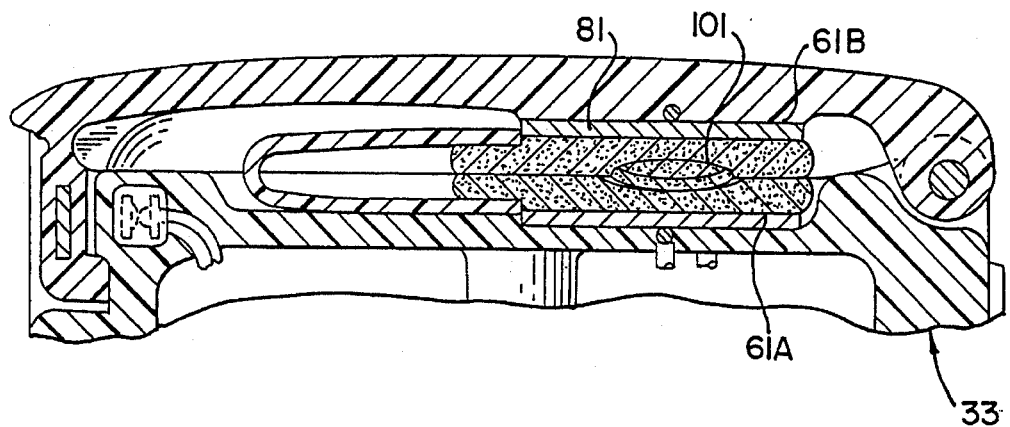
FIG. 5 illustrate in sectional view a lens encased in one embodiment of a protective encasement packet that is contacted on either side between the charge transmitting areas of a cleaning assembly according to the present invention.
Figure 6:
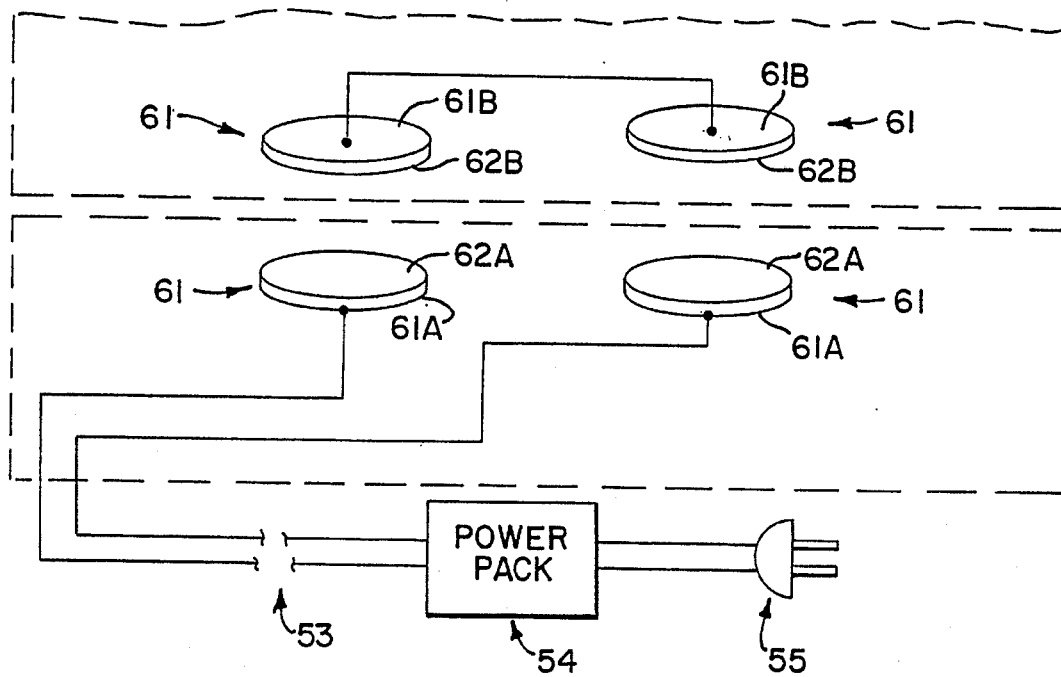
FIG. 6 is a schematic diagram of one embodiment of the circuitry of the cleaning system.

The cleaning assembly illustrated in FIGS. 1 through 6 shows an embodiment in which the surfaces 62A, 62B are generally equal to or greater than the largest diameter of a contact lens 101. In this same embodiment, the charge transmitting surfaces 62 are generally positionable close enough to each other that only a lens encased within a protective encasement packet 81 can be aligned therebetween. Furthermore, a preferred circuit by which each of the two sets of charge transmitting areas 61A, 61B and 62A, 62B are connected in a parallel connection circuit is illustrated in FIG. 6.

Protective encasement packet 81 protects and facilitates the cleaning of a lens 101. More specifically, protective encasement packet 81 is constructed and made from a substance or substances such that the lens can be protectively encased and by which the cleaning of the lens can be facilitated. To protect a lens from damage, the materials of the packet 81 which generally comes into contact with the lens are pliable. Paper, such as ashless paper from which laboratory paper is made, is one such material that is particularly pliable upon moistening. Other suitable substances include formaminous materials such as foam or natural or artificial sponge. Moistening these materials, such as with a solution, allows charges to be efficiently transferred to the lens surface for the electrokinetic cleaning of the lens. A buffered solution is preferred since the production of harmful chemical species is avoided. Preferably, the solution also should be free of sodium or chlorine to avoid the possible production of chemical species that may be harmful to the lens.

Other suitable pliable substances include those which have an appreciable water content and, accordingly, do not require moistening. Such substance include hydrated protein, such as agar, and jelly.

Because some of the substances that are suitable for use in the protective encasement packet 81 by nature have a high water content, or are moist, or the substances are moistened in order to facilitate the transmission of electrical charges, any dehydration of the lens is minimized or entirely avoided. It is known that a fully hydrated hydrogel lens begins to dry immediately upon exposure to the air and that a severely dehydrated lens will lose its flexibility and may crack. However, because a lens may be decontaminated by the present invention advantageously in less time than that required by known apparatus and methods, the charge conducting substance or substances used in the protective encasement packet do not necessarily have to be moistened until fully wetted in order to prevent a lens from becoming harmfully dehydrated. Other substances suitable for use in the packet 81 include material by which electrical charges can be transmitted without moistening. Known charge conducting artificial composite materials are representative of such materials.

The packet 81 may also include materials that aid in the efficient transmission of electrical charges from the charge transmitting surface to the lens 101. Representative of such materials are metal foils.

The packet preferably also includes material that facilitates the retention of contaminants pulled from a lens within the packet and so that they cannot, for example, contaminate the cleaning apparatus. Representative of such material includes known filter or membrane material that can be constructed to slow or prevent altogether the passage of compositions typical of lens contaminants.

Accordingly, protective encasement packet 81 may include one of these substances—such as a foam—or a combination of such substances—such as a sponge with a paper surface—or a composite of such materials—such as one including paper or foam and a charge conducting artificial composite or a sponge or paper backed with metal foil or including metal particles or strips. Other substances, such as jelly, may cover one of the above described substances.

Protective encasement packet 81 is constructed in order to protect and encase and facilitate the cleaning of the lens. For example, packet 81 may be separable into packet sections 83. Each section 83 includes an inner face 84 by which a dominant curved surface of a lens 101 is contacted and covered. The face 84 also may contact a part of or all of the edge area of a lens 101. As in the embodiment of the packet illustrated in FIGS. 4 and 5, the face 84 may be shaped to facilitate contact of the packet 81 with a curved surface and the edge of the lens. The packet 81 may also include sufficiently pliable materials such that the face 84 easily conforms to the curved surface and/or edge area of the lens 101. A packet 81 including a face 84 of such conforming materials and that is of a size larger than the diameter of the largest contact lens generally available will completely conform to the entire curved surface of the lens and beyond.

Because of the preferred generally pliant nature of the substance or substances, from which the packet 81 is made, other elements 85 may be added to define the scope of, support, and/or aid in the alignment of these materials. For example, the embodiment of the protective encasement packet 81 illustrated in FIGS. 4 and 5 includes sections 83 composed of a pliant foam connected by a tab 85. The tab 85 is of a material or materials and structured so that the face 84 of one section 83 can be movably aligned opposite to the face 84 of the other section 83. Tab 85 illustrated in FIGS. 4 and 5 is made of pliant material such as a plastic. Each section or tab 85 may contain means 89 by which a user can identify the packet 81 into which the user placed the left lens and/or the right lens. These identification means 89 may include separate colors, words, and/or symbols, such as shown in FIG. 4, "L" for the packet containing the left eye lens.

Figure 2:
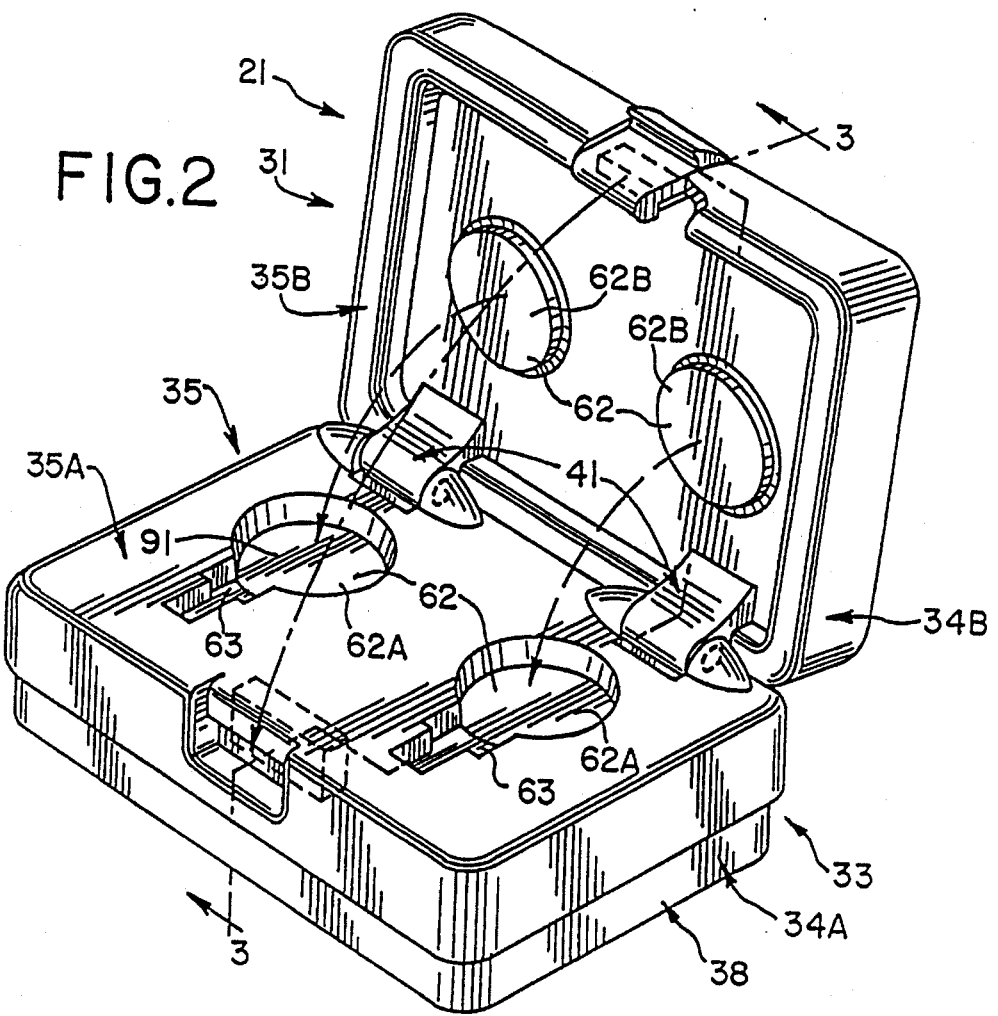
FIG. 2 is a perspective view of the embodiment of the assembly illustrated in FIG. 1 and opened to show the positionable charge transmitting areas exposed from a surface of the assembly.
Figure 3:
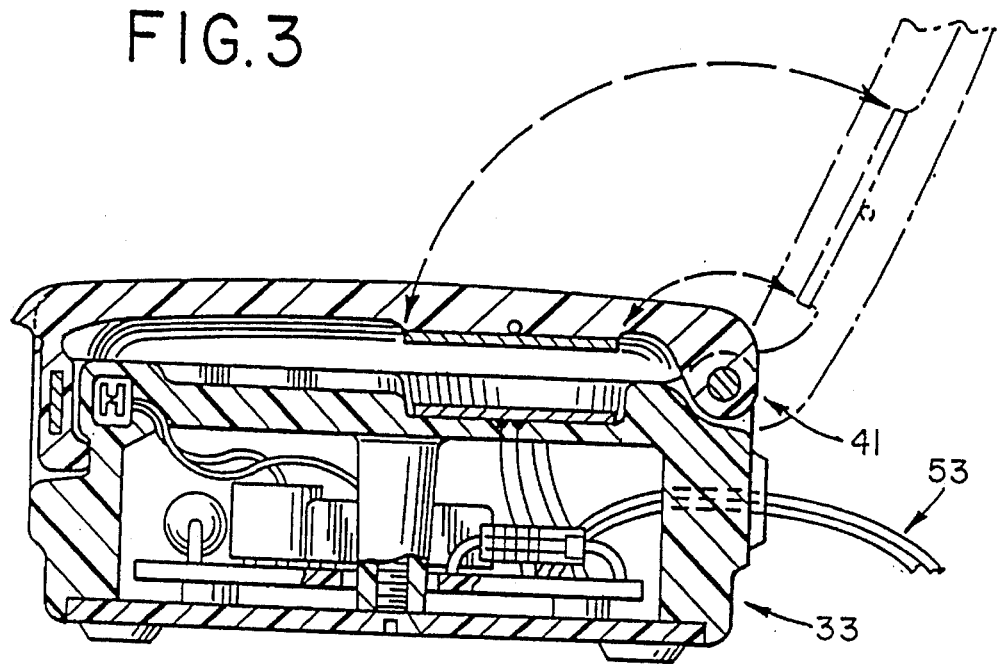
FIG. 3 is a sectional view of the embodiment of the cleaning assembly illustrated in FIG. 1 and FIG. 2 showing the positioning of the housing element in an open position (phantom) and in a closed position.

The system 21 may include means by which, once a lens is placed within the packet, the packet remains aligned even when a charge transmitting surface 62 is brought into contact with an outer face 86 of the packet 81. Such means may include an accommodation space 63 that opens from the surface 35 as illustrated in FIGS. 2, 4, and 5. Once the sections 83 are aligned with the lens 101 therebetween, the packet 81 is placed in contact with the charge transmitting surface 62A. The accommodation space 63 may include a section which is sized and shaped to accommodate the tab 85 of those packets including this feature.

A lens 101 may be decontaminated by the present invention according to the following methods. In those embodiments of the packet 81 in which one or more substance or substance must be moistened to facilitate the transmission of an electrical charge, the substance or substances must be moistened. Each lens 101 to be decontaminated is placed in a packet 81. In the embodiment of the packet 81 illustrated in FIGS. 4 and 5, each lens is placed such that a dominant curved surface is placed completely in contact with a face 84 of a section 83. The other section 83 of the packet 81 is aligned to completely cover the remaining dominant curved face. In the illustrated embodiment of the packet 81, the sections 83 overlap such that the edge of the lens is covered and the sections 83 contact each other. The charge transmitting areas 61 are positioned such that the charge transmitting surfaces 62 of each area 61 contact the outer faces 86 of the packet 81 within which the lens 101 is encased. According to the embodiment of the cleaning assembly illustrated in FIGS. 1 through 6, the outer face 86 of one section 83 of the packet 81 is placed on the surface 62. Tab 85 is placed in the accommodation space 63. Cover 34B is drawn over the packet 81 such that the outer face 86 of the other section 83 of the packet 81 is contacted by surface 62B.

The assembly 31 may include separate means to initiate the charging of the areas 61. For reasons of safety, the closing and opening of the cover 34B may initiate and stop the charging. The electrical charges are transmitted from the surfaces 62, to the outer face 86 of the packet 81, to the substance or substances below the face 86, and onto the surfaces of the lens. Because the face 84 of each section 83 completely surrounds and may extend beyond the edge of the lens 101, the face 84 of each section 83 may contact each other. Despite this overlap, an electrical current is generally established through the lens and not around the lens. This may be due to the fact that the current seeks the path of least resistance which is generally through the lens since it has a generally higher water content than the surrounding substances.

Contaminants absorbed on or trapped within the body of the lens migrates off of and from within the lens under the influence of the charges. Generally within minutes the lens may be decontaminated. With the use of a timer within the system and/or simply by opening the cover of the illustrated embodiment of the assembly 31, the application of electrical charges to the lens or lenses is ceased. The packet 81 with lens 101 encased therein is removed from the assembly. The lens is removed from the packet. Depending on the substance included within the packet 81, the packet may be discarded with contaminants trapped therein or may be cleaned for reuse. Contaminants on the lens, if any remain, may be rinsed away, such as with a solution containing a detergent and rinsed with water. The lens may be returned to the eye.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. Apparatus for removing contaminants from a contact lens of the type having opposed optical surfaces, comprising:

a lens carrier comprising a first charge transmission element adapted to engage one optical surface of the lens, and a second charge transmission element adapted to engage the other optical surface of the lens, said elements being formed of a pliant wetted fluid-absorbing material and being dimensioned to form a compact protective enclosure for the lens;

a housing having a first section including a receptacle for receiving said lens carrier, and a second section closable over said first section and including an engaging surface in registration with said receptacle when said cover sections are joined;

a first electrode in said receptacle in electrical communication with said first charge transmission element when said carrier is seated in said receptacle;

a second electrode on said engaging surface in electrical communication with said second charge transmission element when said carrier is seated in said receptacle and said cover sections are closed; and means including a power supply for establishing current flow between said electrodes whereby contaminants in the lens migrate to said transmission elements.

2. A lens cleaning apparatus as defined in claim 1 wherein said charge transmission elements are hinged together and have substantially the same dimensions.

3. A lens cleaning apparatus as defined in claim 2 wherein said housing sections are hinged together.

4. A lens cleaning apparatus as defined in claim 1 wherein said charge transmission elements are resilient and compressible.

5. A lens cleaning apparatus as defined in claim 4 wherein said engaging surface exerts a compressive force on said lens carrier when said carrier is seated in said receptacle and said housing sections are closed.

6. A lens cleaning apparatus as defined in claim 1 wherein said power supply is contained within said first housing section.

7. A lens cleaning apparatus as defined in claim 1 wherein said current flow is alternating current flow.

8. A lens cleaning apparatus as defined in claim 1 wherein said charge transmission elements are wetted with a saline solution.

9. Apparatus for removing contaminants from a contact lens of the type having opposed optical surfaces, comprising:

a lens carrier comprising charge transmission means for engaging the optical surfaces of said lens, said charge transmission means being formed of a pliant wetted fluid-absorbing material and being dimensioned to form a compact protective carrier for the lens having first and second opposed external surfaces;

a housing for receiving said lens carrier;

a first electrode in said housing in electrical communication with one of said exterior surfaces of said charge transmission means when said carrier is contained within said housing;

a second electrode in said housing in electrical communication with the other of said exterior surfaces of said charge transmission means when said carrier is contained within said housing; and means including a power supply for establishing current flow between said electrodes whereby contaminants in the lens migrate to said transmission elements.

10. A lens cleaning apparatus as defined in claim 9 wherein said housing comprises two hinged housing sections.

11. A lens cleaning apparatus as defined in claim 10 wherein said charge transmission element is resilient and compressible.

12. A lens cleaning apparatus as defined in claim 11 wherein said engaging surface exerts a compressive force on said lens carrier when said carrier is seated in said receptacle and said housing sections are closed.

13. A lens cleaning apparatus as defined in claim 10 wherein said power supply is contained within said first housing section.

14. A lens cleaning apparatus as defined in claim 10 wherein said current flow is alternating current flow.

15. A lens cleaning apparatus as defined in claim 10 wherein said charge transmission elements are wetted with a saline solution.

16. A method for removing contaminants from the optic surfaces of a contact lens, said method comprising the steps of:

(a) protectively encasing a contact lens within a lens carrier, said lens carrier including charge transmission means formed of a pliable porous material by which the optic surfaces of said lens are completely covered, said carrier having opposing outer faces;

(b) positioning said carrier between electrode surfaces, each of said electrode surfaces contacting said opposing outer faces of said carrier; and (c) applying an electric current to said electrodes such that an electrical current is established through said carrier and through said lens protectively encased therein, whereby the contaminants are electrically drawn from said lens and into said carrier.

17. The method according to claim 16, further including the step of alternating the polarity of the electric current.

18. The method according to claim 16 including the additional step of wetting the charge transmission means of the carrier prior to the lens being encased therein.

19. The method according to claim 16, wherein the step of protectively encasing a lens includes protectively encasing a pair of said lenses separately within each of a pair of said carrier, wherein the step of positioning said carrier includes positioning each of said pair of said carriers between a set of said charge transmission elements, and wherein the step of applying an electric current includes applying said electrical current to said opposing outer faces of each of said pair of said carriers such that said electrical current is established through said pair of carriers and said pair of lenses, whereby contaminants are simultaneously removed from said pair of lenses.

20. A method for removing contaminants from the optic surfaces of a contact lens, said method comprising the steps of:

(a) protectively encasing a contact lens within a lens carrier, said lens carrier including a pair of charge transmission elements formed of a wetted porous material engaging respective ones of said optic surfaces, said elements each including an outer face;

(b) positioning said carrier between electrode surfaces, each of said electrode surfaces contacting said opposing outer faces of said carrier; and (c) applying an electric current to said electrodes such that an electrical current is established through said carrier and through said lens protectively encased therein, whereby the contaminants are electrically drawn from said lens to said carrier.

21. The method according to claim 20, further including the step of alternating the polarity of the electric current.

22. The method according to claim 20, wherein the step of protectively encasing a lens includes protectively encasing a pair of said lenses separately within each of a pair of said carriers, wherein the step of positioning said carrier includes positioning each of said pair of said carriers between a set of said charge transmission elements, and wherein the step of applying an electric current includes applying said electrical current to said opposing outer faces of each of said pair of said carriers such that said electrical current is established through said pair of carrier and said pair of lenses, whereby contaminants are simultaneously removed from said pair of lenses.

* * * * *